US00PP25941P3

(12) United States Plant Patent

Ranney et al.

(10) Patent No.: US PP25,941 P3

(45) Date of Patent: Sep. 22, 2015

(54) *HYPERICUM* PLANT NAMED 'NCHC1'

(50) Latin Name: *Hypericum calycinum*
Varietal Denomination: NCHC1

(71) Applicant: North Carolina State University, Raleigh, NC (US)

(72) Inventors: Thomas G. Ranney, Raleigh, NC (US); Darren H. Touchell, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 196 days.

(21) Appl. No.: 13/987,431

(22) Filed: Jul. 24, 2013

(65) Prior Publication Data

US 2015/0033428 P1 Jan. 29, 2015

(51) Int. Cl.
*A01H 5/00* (2006.01)

(52) U.S. Cl.
USPC ..... Plt./442

(58) Field of Classification Search
USPC ..... Plt./442
See application file for complete search history.

(56) References Cited

PUBLICATIONS

Flowering Shrubs, Spring Meadow Nursery, Inc. Starter Plants catalog and Shrub Reference 2012-2013; Sep. 12, 2012, pp. 1, 2, 14 and 51.*
Pluto Plant Variety Database Mar. 6, 2015. p. 1.*
Plant Breeders' Rights Application filed in Canada on Sep. 12, 2012.
United States Postal Service Bulk Mailing Sheet for 2012/2013 Spring Meadows Nursery Catalogue (Sep. 7, 2012).

* cited by examiner

*Primary Examiner* — Annette Para
(74) *Attorney, Agent, or Firm* — Myers Bigel Sibley & Sajovec, PA

(57) ABSTRACT

'NCHC1' is a new *Hypericum calycinum* variety having golden yellow foliage that matures to a light green and does not revert to dark green foliage.

4 Drawing Sheets

Latin name of the genus and species: The Latin name of the novel plant variety disclosed herein is *Hypericum calycinum.*

Variety denomination: The inventive variety of *Hypericum calycinum* disclosed herein has been given the varietal denomination 'NCHC1'.

BACKGROUND OF THE INVENTION

The present invention comprises a new and distinct variety of *hypericum*, botanically known as *Hypericum calycinum*, and hereinafter referred to by the cultivar name 'NCHC1'. This new *hypericum* was developed and selected at North Carolina State University, Mills River, N.C.

*Hypericum calycinum* 'NCHC1' was developed in vitro by inducing somatic embryogenesis from yellow leaves of *Hypericum calycinum* 'Brigadoon'. 'NCHC1' was first established in vitro in 2007 and has been asexually reproduced through micropropagation, division, and stem cuttings at the North Carolina State University, Mountain Horticultural Crops Research Station, Mills River, N.C. over a six year period. 'NCHC1' has been found to retain its distinctive characteristics through successive asexual propagations including the propagation of over 8,000 plants without any reversions to green-leaved phenotypes.

SUMMARY OF THE INVENTION

The following are the unique and distinguishing characteristics of this new cultivar when grown under normal horticultural practices at North Carolina State University, Mountain Horticultural Crops Research Station, Mills River, N.C.

1. A groundcover with persistent (evergreen to semi-evergreen) yellow to chartreuse foliage color; and
2. Does not produce shoots that revert to green foliage colors.

BRIEF DESCRIPTION OF THE DRAWINGS

This new *hypericum* plant is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *Hypericum calycinum*. The photographs were taken in Mills River, N.C.

DETAILED BOTANICAL DESCRIPTION

Figure 1:
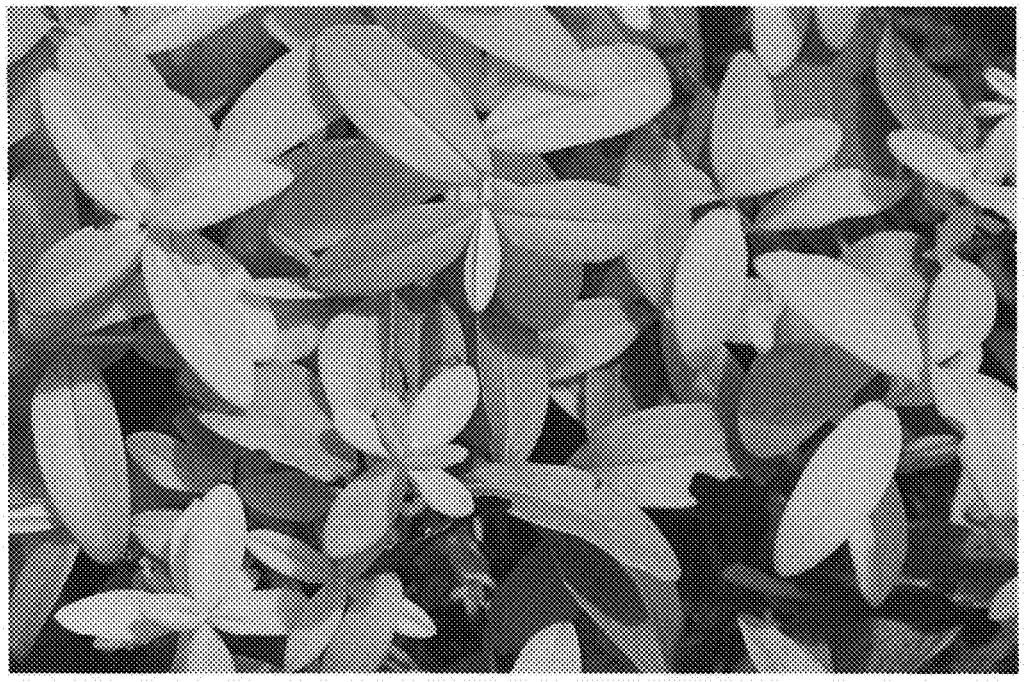
FIG. 1 is a color photograph of young foliage of *Hypericum calycinum* 'NCHC1'.
Figure 2:
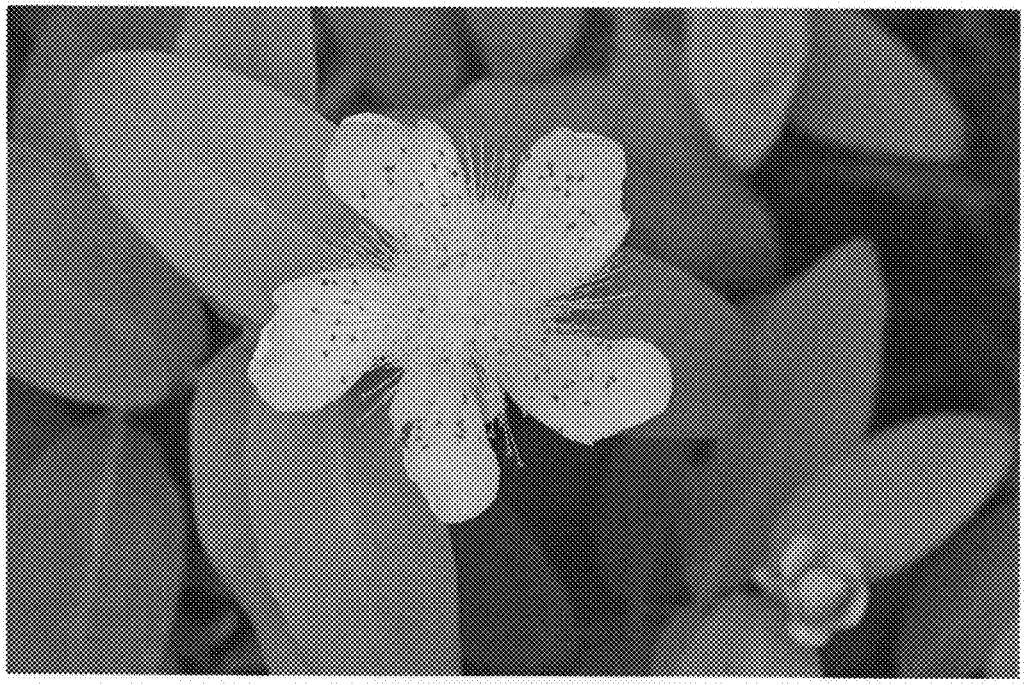
FIG. 2 is a color photograph of the flower and mature foliage of *Hypericum calycinum* 'NCHC1'.
Figure 3:
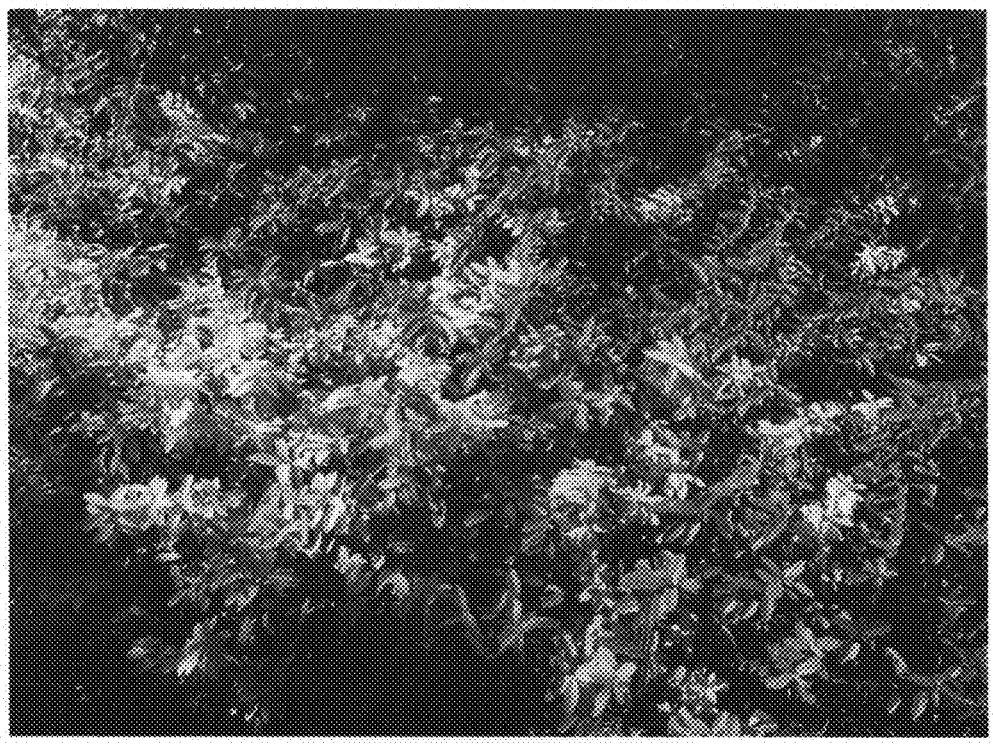
FIG. 3 is a color photograph of an established planting of *Hypericum calycinum* 'Brigadoon' with shoots that have reverted with green foliage.
Figure 4:
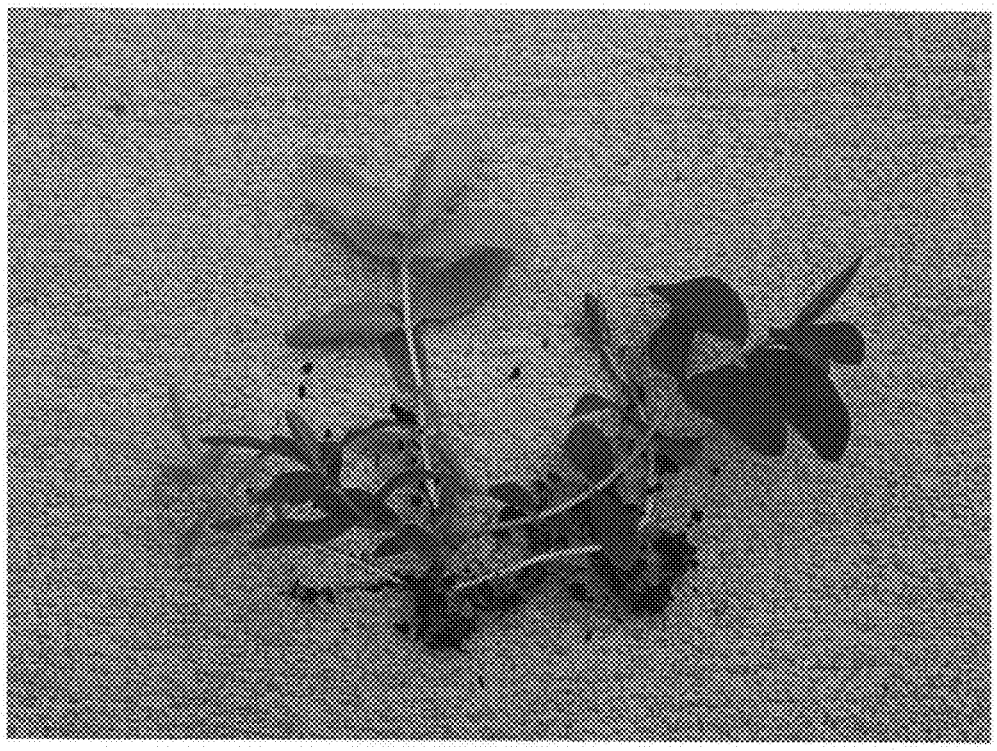
FIG. 4 is a color photograph showing shoots with both yellow and green foliage arising from the same stem on *Hypericum calycinum* 'Brigadoon.'

The following is a detailed description of the botanical characteristics of the new and distinct variety of *Hypericum calycinum* plant known by the denomination 'NCHC1'. The detailed description was taken on two-year-old plants container-grown plants in Mills River, N.C. in July-August of 2012. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

Technical Description of the Variety.

Classification:

*Botanical name.*—*Hypericum calycinum.*

*Common name.*—Aaronsbeard St. Johnswort.

Parentage: Somatic embryo originating from leaves of *Hypericum calycinum* 'Brigadoon'.

Plant description:

*Growth habit.*—Groundcover, procumbent, stoloniferous.

*Height at maturity.*—About 30 cm.

*Width at maturity.*—About 60 cm.

Shoot description:

*Length.*—About 30 cm.

*Diameter.*—About 2 mm.

*Internode length.*—1-2 cm.

*Immature stem color.*—179A.

*Mature stem color.*—178B.

*Texture.*—Smooth, glabrous.

Leaves:

*Type.*—Evergreen to semi-evergreen.

*Arrangement.*—Opposite.

*Shape.*—Elliptic.

*Apex.*—Rounded.

*Base.*—Cuneate.

*Margin.*—Entire.

*Mature leaf size.*—

*Length.*—5 cm.

*Width.*—2 cm.

*Leaf texture.*—Adaxial (upper) surface: smooth, glabrous. Abaxial (lower) surface: smooth, glabrous.

*Immature/developing leaf color.*—Adaxial (upper) surface: ranging from 151A to 1B, margin 47B diffusing throughout leaf to N25A-B. Abaxial (lower) surface: ranging from 151A to 1B, margin and midrib 47B.

*Mature leaf color.*—Adaxial (upper) surface: N144A to 145C. Abaxial (lower) surface: 144C to 145 C.

*Leaf attachment.*—Clasping.

Flowers:

*Type.*—Solitary, cruciform.

*Flowering season.*—Predominately summer — late June through August, with sporadic flowering through fall, in Mills River, N.C.

*Lastingness of flower on the plant.*—3 to 5 days.

*Fragrance.*—Absent.

*Depth at anthesis.*—Average is 3 cm.

*Diameter at anthesis.*—Ranging from 7.5-8.5 cm.

*Self cleaning or persistent.*—Self cleaning.

Petals:

*Number of petals per flower.*—5 in a single whorl.

*Shape.*—Obovate, Apex: obtuse, base: broadly cuneate.

*Color.*—12A at anthesis.

*Surface texture.*—Glabrous (not pubescent).

*Length.*—3.5-4 cm.

*Width.*—1.9-2.3 cm.

Sepals:

*Quantity.*—5.

*Shape.*—Obovate, apex: rounded base: broadly cuneate.

*Arrangement.*—Whorl.

*Length.*—About 20 mm.

*Width.*—About 14 mm.

*Color.*—Adaxial (upper) surface: 145B. Abaxial (lower) surface: 145A.

*Surface texture.*—Glabrous.

Peduncle:

*Length.*—10-15 mm.

*Diameter.*—1.5 mm.

*Color.*—Ranging from 55A to 55B.

Reproductive organs:

*Stamen.*—

*Quantity per flower.*—About 150.

*Anther.*—Shape: ovoid. Color: 181C. Length: about 1 mm. Pollen color: 6A. Pollen amount: abundant.

*Pistil.*—Quantity per flower: 1. Length: 17-23 mm.

*Stigma.*—Shape: Globular. Color: 5D.

*Style.*—Length: 1.5 cm. Color: 154B.

Seeds:

*Length.*—1.5 mm.

*Width.*—Less than 1 mm.

*Color.*—165 A.

Disease and insect resistance: No significant disease or insect pests have been observed.

Comparison with other cultivars: *Hypericum calycinum* 'NCHC1' is distinguished from the similar parental cultivar 'Brigadoon' in that the foliage on 'NCHC1' emerges a golden yellow, matures to a light green and does not revert to dark green foliage like *Hypericum calycinum* 'Brigadoon.'

What is claimed is:

1. A new and distinct variety of *Hypericum calycinum* plant named 'NCHC1,' substantially as illustrated and described herein.

* * * * *